(12) United States Patent
Kellstrom, Jr.

(10) Patent No.: US 12,343,572 B2
(45) Date of Patent: Jul. 1, 2025

(54) ULTRAVIOLET DECONTAMINATING MASK

(71) Applicant: Kellstrom IP Holdings, LLC, Wayne, NJ (US)

(72) Inventor: Gary E. Kellstrom, Jr., Wayne, NJ (US)

(73) Assignee: Kellstrom IP Holdings, LLC, Wayne, NJ (US)

( * ) Notice: Subject to any disclaimer, the term of this patent is extended or adjusted under 35 U.S.C. 154(b) by 881 days.

(21) Appl. No.: 17/222,407

(22) Filed: Apr. 5, 2021

(65) Prior Publication Data

US 2021/0308500 A1    Oct. 7, 2021

Related U.S. Application Data

(60) Provisional application No. 63/055,562, filed on Jul. 23, 2020, provisional application No. 63/004,952, filed on Apr. 3, 2020.

(51) Int. Cl.
*A62B 18/10* (2006.01)
*A41D 13/11* (2006.01)
(Continued)

(52) U.S. Cl.
CPC .............. *A62B 18/10* (2013.01); *A41D 13/11* (2013.01); *A61L 9/20* (2013.01); *A62B 23/00* (2013.01);
(Continued)

(58) Field of Classification Search
CPC .......... A62B 18/00–10; A62B 7/10–12; A62B 9/00–06; A62B 23/00–06; A61L 9/20–205; A61L 2209/14
(Continued)

(56) References Cited

U.S. PATENT DOCUMENTS

| 11,000,624 B1* | 5/2021 | Babcock ................... A61L 9/20 |
| 2007/0102280 A1* | 5/2007 | Hunter ................. B01D 53/007 |
| | | 422/186.3 |

(Continued)

FOREIGN PATENT DOCUMENTS

| CN | 102716556 | 10/2012 |
| CN | 111053979 | 4/2020 |

(Continued)

OTHER PUBLICATIONS

International Preliminary Report on Patentability in International Application No. PCT/US2021/025766, mailed on Oct. 13, 2022, 8 pages.

(Continued)

*Primary Examiner* — Valerie L Woodward
*Assistant Examiner* — Paige Kathleen Bugg
(74) *Attorney, Agent, or Firm* — Fish & Richardson P.C.

(57) ABSTRACT

An inlet chamber defines a flow passage leading into a breathing chamber. A first check valve is located between the inlet chamber and the breathing chamber. The first check valve is configured to allow air flow from the inlet chamber into the breathing chamber. A second check valve is located between the breathing chamber and an exhaust chamber. The second check valve is configured to allow air flow from the breathing chamber into the exhaust chamber. An ultraviolet light source is configured to administer a dose of ultraviolet light sufficient to decontaminate gas flowing through either the inlet chamber, the exhaust chamber, or both.

22 Claims, 5 Drawing Sheets

(51) Int. Cl.
*A61L 9/20* (2006.01)
*A62B 23/00* (2006.01)

(52) U.S. Cl.
CPC ....... *A61L 2209/12* (2013.01); *A61L 2209/14* (2013.01)

(58) Field of Classification Search
USPC .................................................... 128/205.24
See application file for complete search history.

(56) References Cited

U.S. PATENT DOCUMENTS

| | | | | |
|---|---|---|---|---|
| 2012/0279503 | A1* | 11/2012 | Zhou | A41D 13/1192 128/205.27 |
| 2016/0067441 | A1* | 3/2016 | Bearne | A61M 16/06 128/205.25 |
| 2020/0121005 | A1* | 4/2020 | Belousov | A41D 13/1107 |
| 2021/0275714 | A1* | 9/2021 | Almeida | A62B 18/025 |
| 2021/0361818 | A1* | 11/2021 | Almeida | A62B 18/025 |

FOREIGN PATENT DOCUMENTS

| | | | |
|---|---|---|---|
| CN | 211835880 | 11/2020 | |
| WO | WO-02076517 A1 * | 10/2002 | ............ A61L 2/0011 |
| WO | WO 2008/120005 | 10/2008 | |
| WO | WO-2008120005 A1 * | 10/2008 | ......... A41D 13/1192 |
| WO | WO-2021018436 A1 * | 2/2021 | ........... A61F 7/0085 |

OTHER PUBLICATIONS

International Search Report and Written Opinion in International Application No. PCT/US2021/025766, dated Jul. 30, 2021, 14 pages.

Extended European Search Report in European Application No. 24164588.8, dated Jun. 20, 2024, 7 pages.

* cited by examiner

ULTRAVIOLET DECONTAMINATING MASK

CROSS-REFERENCE TO RELATED APPLICATIONS

This application claims priority to U.S. Provisional Application Ser. No. 63/004,952, filed on 3 Apr. 2020, and U.S. Provisional Application Ser. No. 63/055,562, filed on 23 Jul. 2020, both of which are incorporated into the present disclosure by reference.

TECHNICAL FIELD

This disclosure relates to personal protective equipment and medical devices.

BACKGROUND

When dealing with infectious diseases, medical personal often wear personal protection equipment (PPE) to prevent inhaling pathogens from infected patients and exhaling pathogens to susceptible patients and medical personnel. An example PPE is an N95 filter mask. Such a mask fits securely over the nose and mouth and has sufficient filtration to stop pathogens from crossing through the mask. To maintain sanitary practices, such PPE is often discarded after one use to ensure there is no cross contamination between patients and personnel.

SUMMARY

This disclosure relates to an ultraviolet decontaminating mask.

An example implementation of the subject matter within this disclosure is a protective mask with the following features. An inlet chamber defines a flow passage leading into a breathing chamber. A first check valve is located between the inlet chamber and the breathing chamber. The first check valve is configured to allow air flow from the inlet chamber into the breathing chamber. A second check valve is located between the breathing chamber and an exhaust chamber. The second check valve is configured to allow air flow from the breathing chamber into the exhaust chamber. An ultraviolet light source is configured to administer a dose of ultraviolet light sufficient to decontaminate gas flowing through either the inlet chamber or the exhaust chamber.

Aspects of the example protective mask, that can be combined with the example mask alone or in combination with other aspects, include the following. An inlet filter is positioned at an inlet of the inlet chamber.

Aspects of the example protective mask, that can be combined with the example mask alone or in combination with other aspects, include the following. The exhaust chamber includes a helical flow passage surrounding the ultraviolet light source. An inlet passage is arranged such that ultraviolet light emitted from the ultraviolet light source is not exposed to skin of a protective mask wearer.

Aspects of the example protective mask, that can be combined with the example mask alone or in combination with other aspects, include the following. The ultraviolet light source includes a light emitting diode.

Aspects of the example protective mask, that can be combined with the example mask alone or in combination with other aspects, include the following. The ultraviolet light source includes mercury lamps with quartz-doped globes or tubes.

Aspects of the example protective mask, that can be combined with the example mask alone or in combination with other aspects, include the following. The exhaust chamber is a first exhaust chamber, wherein the protective mask further includes a second exhaust chamber.

Aspects of the example protective mask, that can be combined with the example mask alone or in combination with other aspects, include the following. The exhaust chamber is arranged such that little to no moment is exerted against a wearer of the protective mask.

Aspects of the example protective mask, that can be combined with the example mask alone or in combination with other aspects, include the following. A second ultraviolet light source is configured to administer a dose of ultraviolet light sufficient to decontaminate air flowing through the inlet chamber.

An example implementation of the subject matter described within this disclosure is a protective mask with the following features. An inlet chamber defines a flow passage leading into an accumulation chamber. A first ultraviolet light source is configured to administer a dose of ultraviolet light sufficient to decontaminate air flowing through the inlet chamber. A breathing chamber is configured to enclose a user's nose and mouth. A first check valve is located between the accumulation chamber and the breathing chamber. The first check valve is configured to allow air flow from the accumulation chamber into the breathing chamber. A second check valve is located between the breathing chamber and an exhaust chamber. The second check valve is configured to allow air flow from the breathing chamber into the exhaust chamber.

Aspects of the example protective mask, that can be combined with the example mask alone or in combination with other aspects, include the following. The inlet chamber includes a helical flow passage surrounding the ultraviolet light source, and an inlet passage arranged such that ultraviolet light emitted from the ultraviolet light source is not exposed to skin of a protective mask wearer.

Aspects of the example protective mask, that can be combined with the example mask alone or in combination with other aspects, include the following. The chamber is a first chamber, the protective mask further comprising a second chamber.

Aspects of the example protective mask, that can be combined with the example mask alone or in combination with other aspects, include the following. A second ultraviolet light source is configured to administer a dose of ultraviolet light sufficient to decontaminate air flowing through the exhaust chamber.

Aspects of the example protective mask, that can be combined with the example mask alone or in combination with other aspects, include the following. An inlet filter is positioned at an inlet of the inlet chamber.

Aspects of the example protective mask, that can be combined with the example mask alone or in combination with other aspects, include the following. The exhaust chamber includes a helical flow passage surrounding the ultraviolet light source, and an inlet passage arranged such that ultraviolet light emitted from the ultraviolet light source is not exposed to skin of a protective mask wearer.

An example implementation of the subject matter described within this disclosure is a method with the following features. Exhaled air is received from a user. The exhaled air is disinfected. The disinfected air is emitted to a surrounding environment.

Aspects of the example method, that can be combined with the example method alone or in combination with other aspects, include the following. Disinfecting includes emitting a dose of ultraviolet radiation to the exhaled air. The dose is sufficient to disinfect the exhaled air to a level sufficient to reduce transmission of infection.

Aspects of the example method, that can be combined with the example method alone or in combination with other aspects, include the following. A user's skin is shielded from the emitted dose of ultraviolet radiation.

Aspects of the example method, that can be combined with the example method alone or in combination with other aspects, include the following. Fresh air is received. The fresh air is treated prior to the fresh air being inhaled.

Aspects of the example method, that can be combined with the example method alone or in combination with other aspects, include the following. Treating includes removing particulates by a filter.

Aspects of the example method, that can be combined with the example method alone or in combination with other aspects, include the following. Treating includes disinfecting the air by ultraviolet radiation.

Other features, objects, and advantages of the subject matter will be apparent from the description and drawings, and from the claims.

DESCRIPTION OF DRAWINGS

Like reference symbols in the various drawings indicate like elements.

DETAILED DESCRIPTION

This disclosure describes a protective mask that can be used to reduce an exchange of pathogens between individuals. Such a protective mask can include a filter or other decontamination mechanism on an inlet and can also include a decontamination mechanism on an outlet. As a result, clean, decontaminated air is breathed in by the user, and the exhaled air is decontaminated before being introduced into the surrounding environment. Such a device allows infected individuals to maintain their lifestyle and prevent (e.g. fully prevent or reduce the likelihood of) them from contaminating other individuals that they may interact with. In addition, in implementations where a filter or other decontamination mechanism is used on the inlet, such a device allows susceptible individuals to interact with those that are infected without fear of becoming infected themselves.

Figure 1:
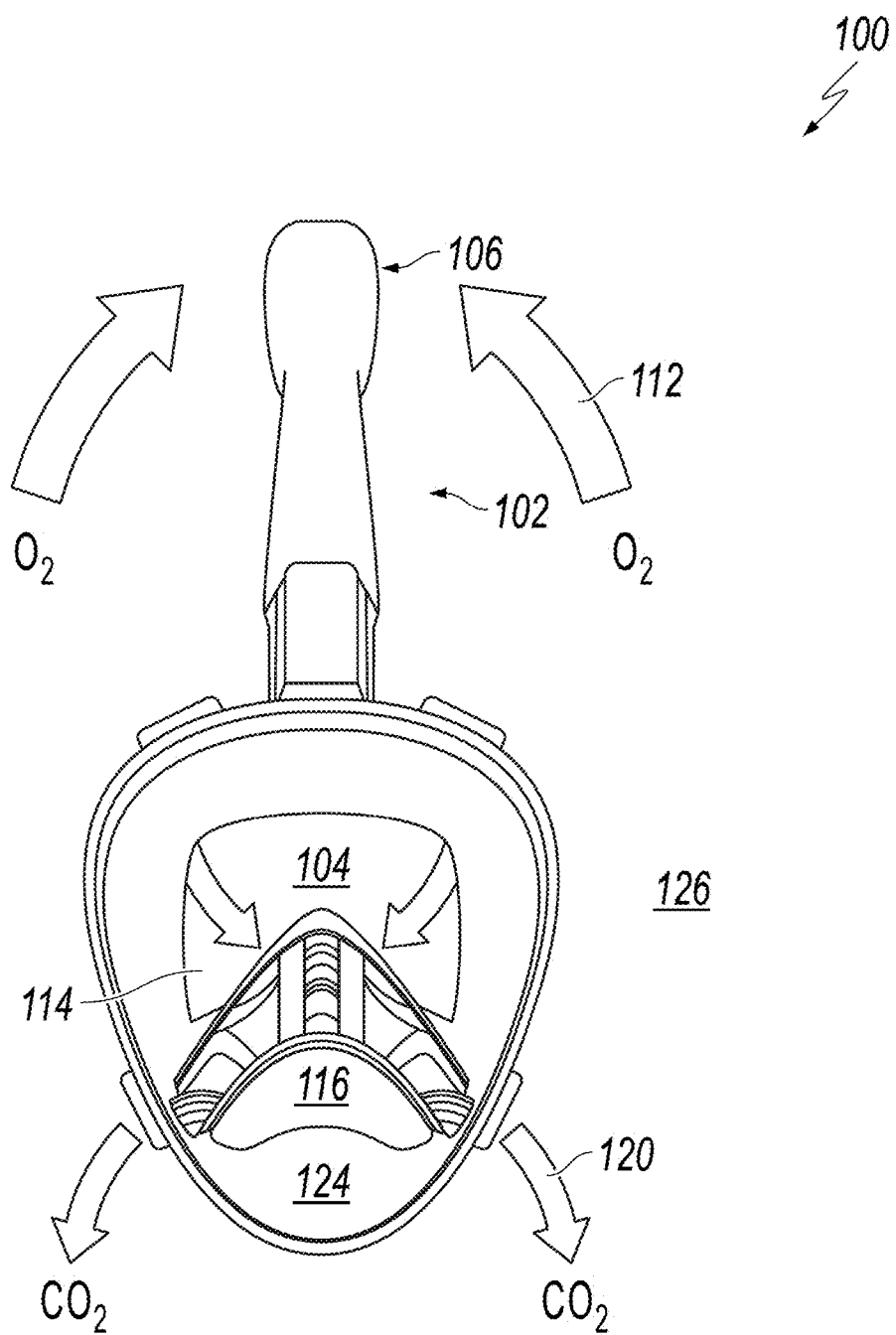
FIG. 1 is a front view of an example protective mask.
Figure 2:
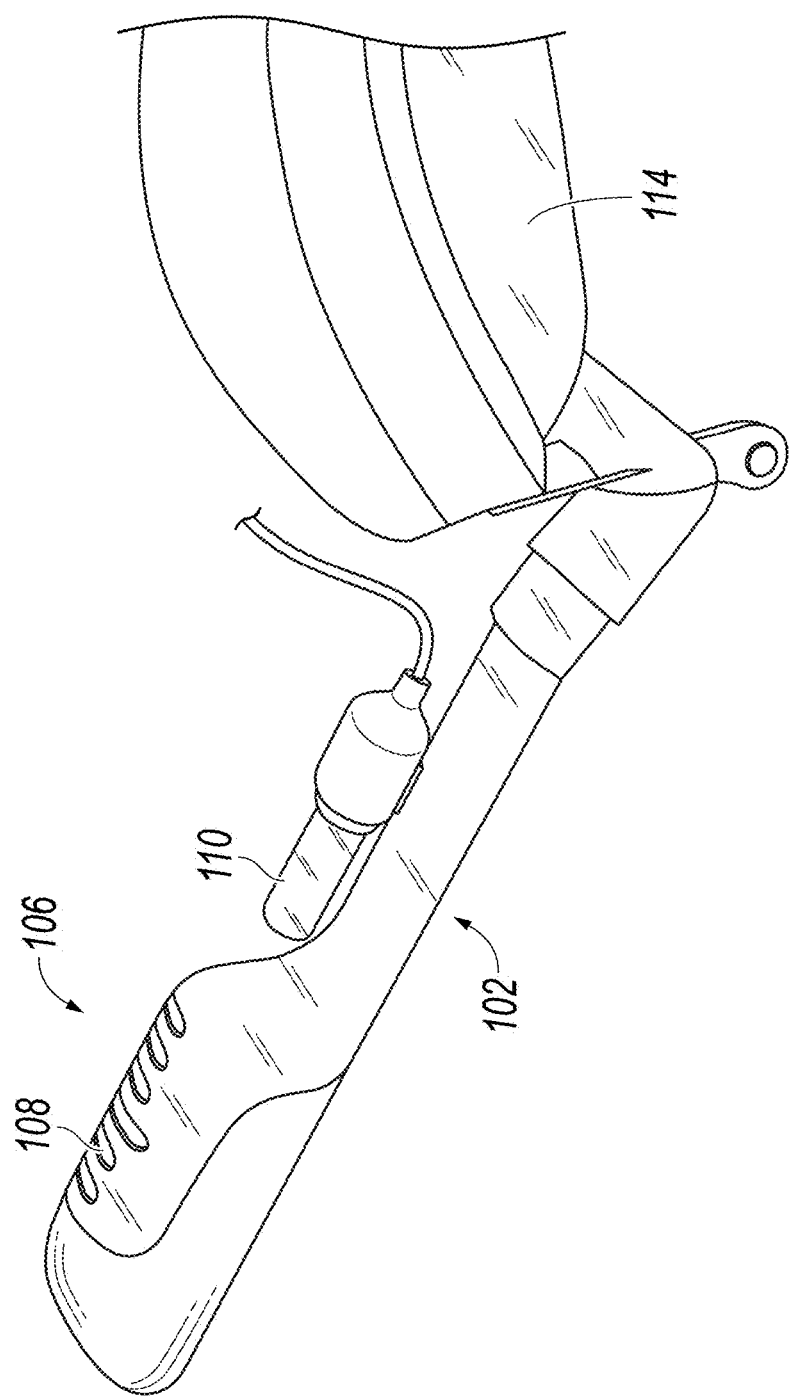
FIG. 2 is a side view of the inlet chamber of the example protective mask.
Figure 3:
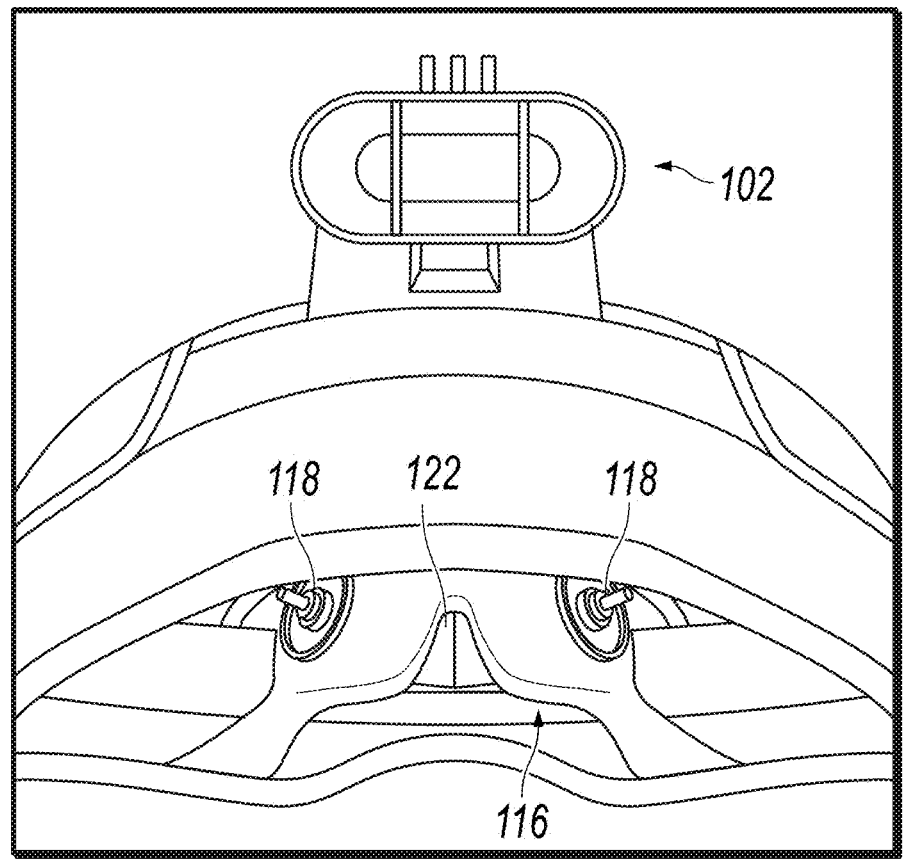
FIG. 3 is a top-down view of the example protective mask.

FIG. 1 is a front view of an example protective mask 100. FIG. 2 is a side view of the inlet chamber of the example protective mask. FIG. 3 is a top-down view of the example protective mask. The description herein is given in context of FIGS. 1-3.

The protective mask 100 includes an inlet chamber 102 that defines a flow passage leading into an accumulation chamber 104. In some implementations, an inlet 106 of the inlet chamber 102 has an inlet filter 108. The inlet filter 108 can be an antimicrobial or anti-viral filter, such as that used in an N95 filter.

Alternatively or in addition, in some implementations there is an ultra violet (UV) light source 110 configured to emit UV light into the inlet chamber 102. The UV light source 110 can be battery powered. Both the inlet chamber 102 and the UV light source 110 are configured to disinfect any fresh air 112 (air from the surrounding environment) flowing through the inlet chamber 102 before the air 112 is inhaled in by user. The dosage of UV light is dependent upon the wattage of the UV light source 110, the proximity of the UV light source to air 112 within the inlet chamber 102, and the exposure/retention time of air 110 within the inlet chamber 102. In general, all of these factors are used to ensure a sufficient dosage of UV light decontaminate the air 112. For example, the inlet chamber 102 may define a serpentine passage to allow for a greater retention of air 112 within the inlet chamber 102. The greater retention time effectively increases the dosage of UV light. In general, the UV light source 110 and the inlet chamber 102 are configured to decontaminate the air 112 at a sufficient rate for a normally breathing individual. For example, a normally breathing individual can inhale/exhale approximately 0.5 Liters (L) or air per breath. The volume of air per breath is often referred to as a "tidal volume" and varies somewhat between individuals based on a variety of factors, such as height and weight. In some implementations, the UV light source 110 and the inlet chamber 102 are configured to decontaminate up to four times the estimated tidal volume or air-flow rate of air required by a user. This safety margin allows for changes in breathing patterns, for example, when a user is active and or exerting themselves more than usual.

The UV light source 110 typically emits a wavelength of approximately 254 nanometers (nm) (+ or −10%); however, certain UV light sources, such as mercury bulbs, can also emit a wavelength at approximately 185 nm. The 185 nm wavelength produces ozone, which is harmful if breathed in by the user. To mitigate this concern, a catalyst can be included within the chamber 102. For example, titanium dioxide ($TiO_2$) can be used within the inlet chamber 102. In such an implementation, there is sufficient $TiO_2$ surface area to be able to fully catalyze the ozone ($O_3$) back into oxygen ($O_2$), which is safe to inhale. Such implementations can include a $TiO_2$ coating along an inner surface of the chamber 102. In some implementations, a mesh or honeycomb-like insert coated with $TiO_2$ can be located within the chamber 102 in order to increase the surface area of $TiO_2$.

In some implementations, a precise UV light source 110 can be used. In such implementations, only 254 nm wavelength light is emitted, and as such, ozone is not produced and the catalyst is not required. Such UV light sources can include LEDs and mercury lamps than include quartz-doped globes and/or tubes. As UV light can cause burns on human skin, the inlet chamber 102 and the UV light source 110 are configured to block UV light from being exposed to the skin of the user and anyone in proximity to the user.

After the air 112 has passed through the inlet chamber 102, the air 112 enters an accumulation chamber 104. As illustrated, the accumulation chamber 104 is behind a face shield 114 in front of the user's eyes. In some implementations of face shield 114 is not used, and the inlet chamber is connected directly to a breathing chamber 116. The breathing chamber and the transition into the breathing chamber will be discussed later within this disclosure.

From the accumulation chamber 104, fresh air passes into the breathing chamber 116. To go from the accumulation chamber 104 to the breathing chamber 116, the air 110 passes through at least one check valve 118 positioned between the accumulation chamber 104 and the breathing chamber 116. As illustrated, two check valves 118 are present. Any type of check valve with sufficient sealing and flow characteristics can be uses, for example, a reed valve. This check valve 118 only allows air 112 to flow one-way through the check valve 118: from the accumulation chamber 104 to the breathing chamber 116. As such, as the user inhales, air passes from the accumulation chamber 104, through the check valve(s) 118, and into the breathing chamber 116. Once in the breathing chamber 116, the air 112 can be inhaled into the user's lungs. Once the user exhales, the check valve(s) 118 close, and the exhaled air 120 is unable to flow back into accumulation chamber 104.

Instead, the exhaled air 120 passes through a second check valve 122 into an exhaust chamber 124. The second check valve 122 is also a one-way valve that only allows the exhaled air 120 to pass from the breathing chamber 116 into the exhaust chamber 124. The exhaust chamber 124, in some implementations, has a second UV light source (not shown). The second UV light source decontaminates the exhaled air 120 exhaled from the user. The exhaust chamber 124 and the second UV light source are both configured to supply a sufficient dosage of UV light to the exhaled air 120 to decontaminate the exhaled air 120 before it is released to the surrounding environment 126. In addition, the exhaust chamber 124 and the second UV source are configured to prevent UV light from touching the skin. Decontaminating the exhaled air 120 allows for the user to continue interactions with susceptible individuals without fear of infecting other individuals around the user. While the exhaled air 120 does not back-flow into the breathing chamber, precautions can be taken to ensure that any ozone produced by the second UV light source is reduced. As previously described in the context of the inlet chamber 102, a precise UV light source and/or a TIO$_2$ catalyst can be used within the exhaust chamber to reduce ozone levels in the exhaled air 120. Such a precaution allows the protective mask 100 to be used in an enclosed space without increasing ozone levels with the enclosed space to dangerous levels. In some implementations, only exhaled air is exposed to a UV light source.

Figure 4:
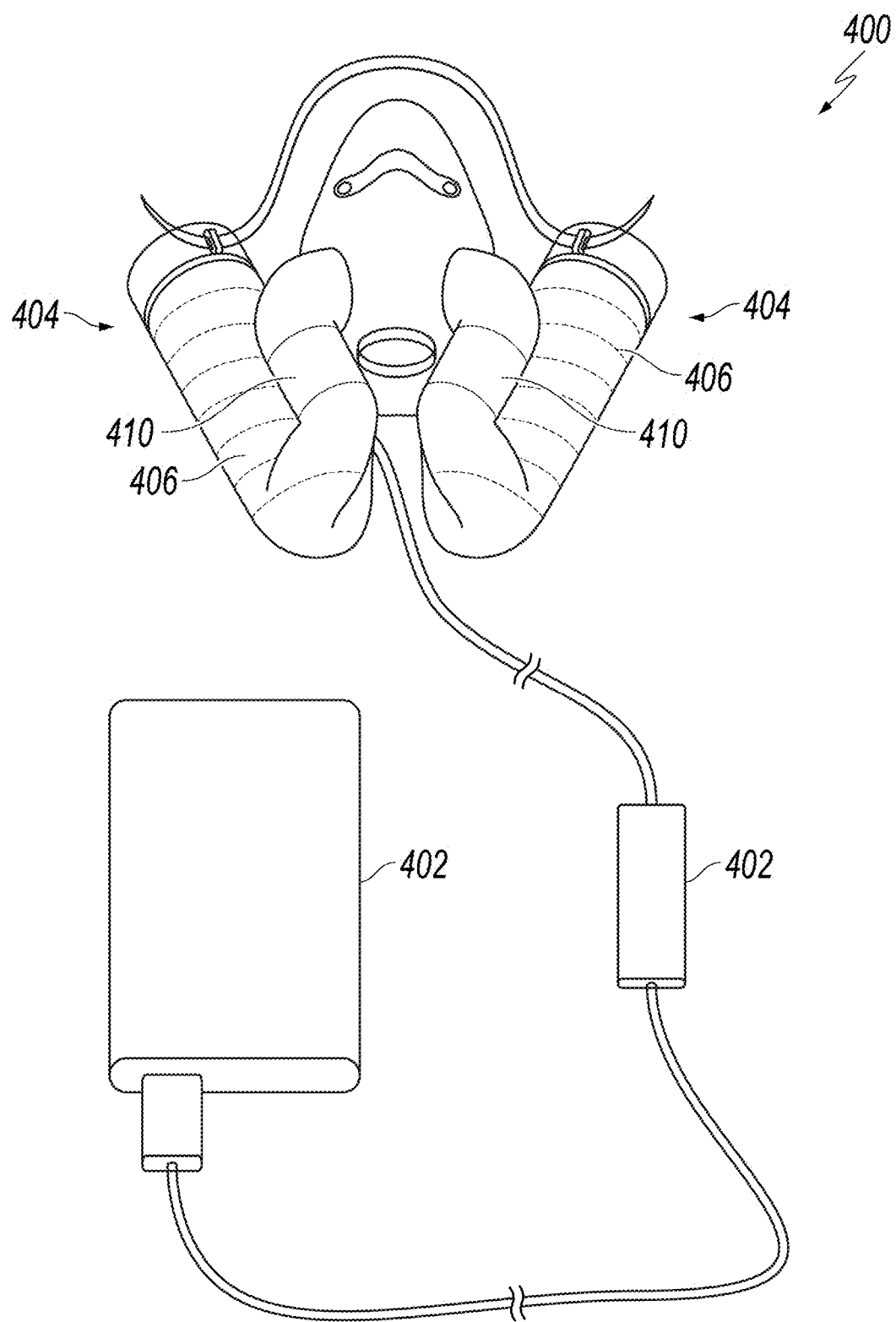
FIG. 4 is an example protective mask with a battery pack connected.
Figure 5:
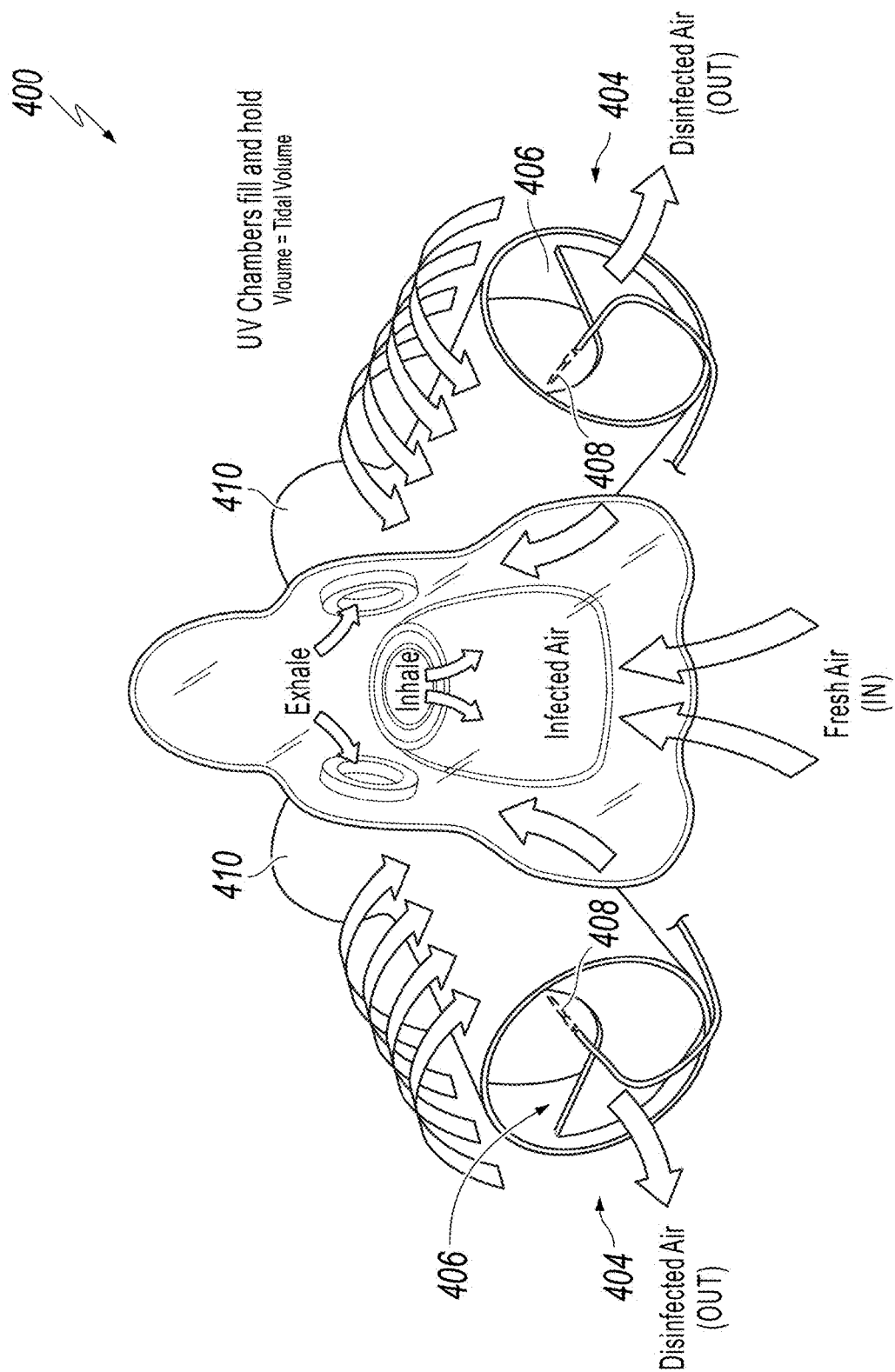
FIG. 5 is a schematic diagram of an example protective mask with annotated airflows.

FIG. 4 is an example protective mask 400 with a battery pack 402 connected. In some implementations, additional control and power conditioning circuitry 403 can be included to drive the ultraviolet light source 408. FIG. 5 is a schematic diagram of an example protective mask 400 with annotated airflows. In the illustrated implementation, the exhaust chamber 404 includes a helical flow passage 406 surrounding the ultraviolet light source 408, and an inlet passage 410 arranged such that ultraviolet light emitted from the ultra violet light source 408 does not contact skin of the wearer. In some implementations, the exhaust chamber 404 can be arranged such that the exhaust chamber is substantially balanced. That is, the exhaust chamber is arranged such that the weight/balance of the exhaust chamber does not create a moment on the mask 400 significant enough to cause excessive discomfort to the wearer.

While primarily illustrated as a complete unit, the concepts described herein can be applied in whole or in part with other, off the shelf components. For example, helical exhaust chambers and ultraviolet light sources described herein can be attached to a standard ventilator mask without departing from this disclosure. The idea of decontaminating exhaled or exhaust air can be applied to other medical devices as well. For example, ventilators and respirators, in addition to or in lieu of using exhaust filters, can instead use these exhaust chambers with a UV light source to decontaminate any air that may be contaminated with pathogens.

While this disclosure contains many specific implementation details, these should not be construed as limitations on the scope of what may be claimed, but rather as descriptions of features specific to particular implementations. Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the implementations previously described should not be understood as requiring such separation in all implementations, and it should be understood that the described components and systems can generally be integrated together in a single product or packaged into multiple products.

A number of implementations of the subject matter have been described. Nevertheless, it will be understood that various modifications may be made without departing from the spirit and scope of the subject matter. For example, aspects of this disclosure are applicable to ventilators and respirators as well. Accordingly, other implementations are within the scope of the following claims. Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

What is claimed is:

1. A protective mask comprising:
 a breathing chamber;
 an inlet chamber defining a flow passage leading into the breathing chamber;
 a first check valve between the inlet chamber and the breathing chamber, the first check valve configured to allow air flow from the inlet chamber into the breathing chamber;
 an exhaust chamber comprising a helical flow passage surrounding an ultraviolet light source, the ultraviolet light source suspended in the exhaust chamber along the helical flow passage, the exhaust chamber comprising a substantially cylindrical surface and a helical surface disposed radially within the cylindrical surface along a length of the exhaust chamber, the cylindrical surface and the helical surface defining the helical flow passage;
 a second check valve between the breathing chamber and the exhaust chamber, the second check valve configured to allow air flow from the breathing chamber into the exhaust chamber;
 the ultraviolet light source configured to administer a dose of ultraviolet light sufficient to decontaminate gas flowing through the exhaust chamber.

2. The protective mask of claim 1, further comprising an inlet filter positioned at an inlet of the inlet chamber.

3. The protective mask of claim 1, wherein the exhaust chamber comprises:
an inlet passage arranged such that ultraviolet light emitted from the ultraviolet light source is configured to avoid exposure to skin of a wearer of the protective mask.

4. The protective mask of claim 3, wherein the ultraviolet light source comprises a light emitting diode.

5. The protective mask of claim 3, wherein the ultraviolet light source comprises mercury lamps with quartz-doped globes or tubes.

6. The protective mask of claim 1, wherein the exhaust chamber is a first exhaust chamber, wherein the protective mask further comprises a second exhaust chamber.

7. The protective mask of claim 1, wherein the exhaust chamber is configured to be arranged such that little to no moment is exerted against a wearer of the protective mask.

8. The protective mask of claim 1, wherein the ultraviolet light source is a first ultraviolet light source configured to administer the dose of ultraviolet light to the exhaust chamber, the protective mask further comprising a second ultraviolet light source configured to administer a second dose of ultraviolet light sufficient to decontaminate air flowing through the inlet chamber.

9. A protective mask comprising:
an inlet chamber defining a flow passage leading into an accumulation chamber;
a first ultraviolet light source configured to administer a dose of ultraviolet light sufficient to decontaminate air flowing through the inlet chamber;
a breathing chamber configured to enclose a user's nose and mouth, the accumulation chamber interposed between the inlet chamber and the breathing chamber in a direction of the air flow;
a first check valve between the accumulation chamber and the breathing chamber, the first check valve configured to allow air flow from the accumulation chamber into the breathing chamber;
an exhaust chamber comprising a helical flow passage surrounding a second ultraviolet light source, the second ultraviolet light source suspended in the exhaust chamber along the helical flow passage, the exhaust chamber comprising a substantially cylindrical surface and a helical surface disposed radially within the cylindrical surface along a length of the exhaust chamber, the cylindrical surface and the helical surface defining the helical flow passage; and
a second check valve between the breathing chamber and the exhaust chamber, the second check valve configured to allow air flow from the breathing chamber into the exhaust chamber.

10. The protective mask of claim 9, wherein the inlet chamber comprises:
a helical flow passage surrounding the first ultraviolet light source; and
an inlet passage arranged such that ultraviolet light emitted from the first ultraviolet light source is configured to avoid exposure to skin of a wearer of the protective mask.

11. The protective mask of claim 9, wherein the exhaust chamber is a first exhaust chamber, the protective mask further comprising a second exhaust chamber.

12. The protective mask of claim 9, wherein the second ultraviolet light source is configured to administer a dose of ultraviolet light sufficient to decontaminate air flowing through the exhaust chamber.

13. The protective mask of claim 9, further comprising an inlet filter positioned at an inlet of the inlet chamber.

14. The protective mask of claim 9, wherein the exhaust chamber comprises:
an inlet passage arranged such that ultraviolet light emitted from the second ultraviolet light source is configured to avoid exposure to skin of a wearer of the protective mask.

15. A method comprising:
receiving, at an exhaust chamber of a protective mask, exhaled air from a user, the exhaust chamber comprising a helical flow passage, the exhaust chamber comprising a substantially cylindrical surface and a helical surface disposed radially within the cylindrical surface along a length of the exhaust chamber, the cylindrical surface and the helical surface defining the helical flow passage;
disinfecting, with ultraviolet radiation from an ultraviolet light source, the exhaled air in the exhaust chamber, the ultraviolet light source suspended in the exhaust chamber along the helical flow passage, and the helical flow passage surrounding the ultraviolet light source; and
emitting the disinfected air to a surrounding environment.

16. The method of claim 15, wherein disinfecting the exhaled air comprises:
emitting a dose of the ultraviolet radiation to the exhaled air, the dose being sufficient to disinfect the exhaled air to a level sufficient to reduce transmission of infection.

17. The method of claim 16, further comprising shielding a user's skin from the emitted dose of ultraviolet radiation.

18. The method of claim 15, further comprising:
receiving, at an inlet chamber of the protective mask, fresh air; and
treating the fresh air in the inlet chamber prior to the fresh air being inhaled by the user.

19. The method of claim 18, wherein treating the fresh air comprises removing particulates by a filter connected to the inlet chamber.

20. The method of claim 18, wherein treating the fresh air comprises disinfecting the air by ultraviolet radiation in the inlet chamber.

21. The protective mask of claim 1, wherein the ultraviolet light source comprises a tubular ultraviolet light source disposed within the exhaust chamber along a longitudinal center axis of the helical flow passage.

22. The protective mask of claim 21, wherein the tubular ultraviolet light source comprises one or more mercury lamps with quartz-doped tubes.

* * * * *